United States Patent [19]

Kovar et al.

[11] 3,966,729

[45] June 29, 1976

[54] ADDITION CURABLE PHENYL-QUINOXALINE COMPOSITIONS AND THEIR SYNTHESIS

[75] Inventors: Robert F. Kovar, Dayton; Fred E. Arnold, Centerville, both of Ohio

[73] Assignee: The United States of America as represented by the Secretary of the Air Force, Washington, D.C.

[22] Filed: May 19, 1975

[21] Appl. No.: 578,846

[52] U.S. Cl. ............................ 260/250 Q; 260/47 R; 260/49; 260/50; 260/65
[51] Int. Cl.² ................ C07D 241/42; C07D 241/44
[58] Field of Search ............ 260/250 Q, 250 QN, 50, 260/65

[56] References Cited
UNITED STATES PATENTS
3,876,614  4/1975  Hedberg ............................... 260/50

Primary Examiner—Raymond V. Rush
Assistant Examiner—Mark L. Berch
Attorney, Agent, or Firm—Joseph E. Rusz; Cedric H. Kuhn

[57] ABSTRACT

An aromatic bis(o-diamine) is reacted with an aromatic bisbenzil to provide a benzil end-capped quinoxaline oligomer which is then reacted with 4-(3-ethynylphenoxy)orthophenylene diamine to give an ethynyl terminated polyquinoxaline. Because the polyquinoxalines can be cured to provide thermally stable polymer compositions having superior mechanical properties, the compositions are particularly suitable for use in the fabrication of reinforced composite structures.

6 Claims, 1 Drawing Figure

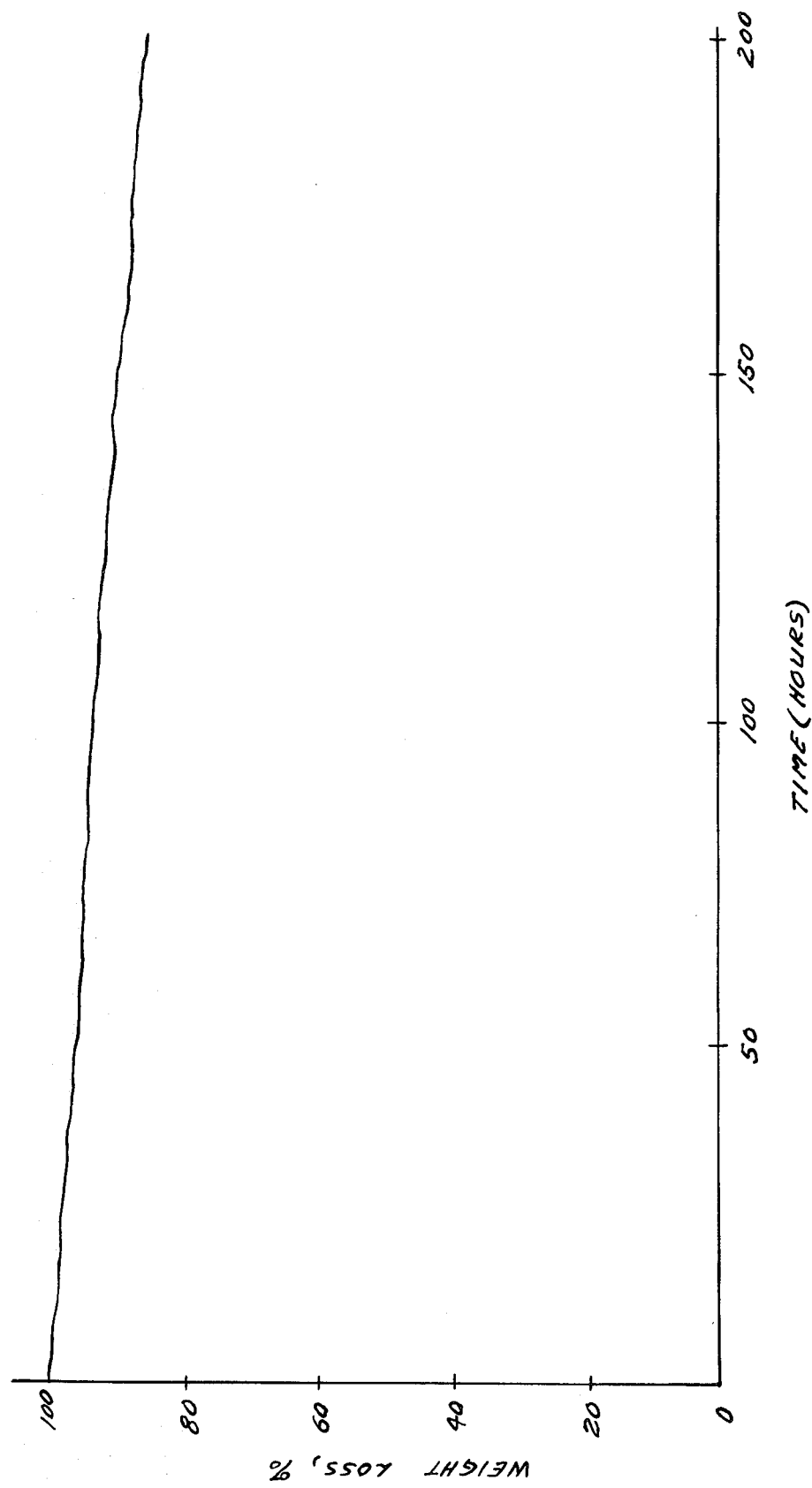

3,966,729

ADDITION CURABLE PHENYL-QUINOXALINE COMPOSITIONS AND THEIR SYNTHESIS

RIGHTS OF THE GOVERNMENT

The invention described herein may be manufactured and used by or for the Government of the United States for all governmental purposes without the payment of any royalty.

FIELD OF THE INVENTION

This invention relates to ethynyl terminated polyquinoxalines. In one aspect it relates to a process for preparing the polyquinoxalines. In still another aspect it relates to the cured polyquinoxalines.

BACKGROUND OF THE INVENTION

Advanced aircraft and aerospace systems demand light weight structures which are dependent upon the availability and effective utilization of superior structural materials. The material requirements are not only for superior mechanical properties, but it is also necessary that the materials possess a high degree of thermal oxidative stability.

The most attractive class of nonmetallic polymeric materials fulfilling both the superior mechanical and thermal stability property requirements are the aromatic heterocyclic polymers. Unfortunately, the most thermally stable systems in this class of materials are formed by condensation reactions with the evolution of by-products. In the fabrication of reinforced composite structure, the volatile by-products, which are evolved, form voids in the structures. As a result of the voids, the structures are greatly weakened, thereby rendering them unsatisfactory for use in aircraft and aerospace systems. Thus, there is a need for a heterocyclic oligomeric material possessing all the required fabrication criteria that can be converted to a thermally stable, high molecular weight polymer by a non-volatile addition reaction.

It is an object of this invention, therefore, to provide quinoxaline oligomers which propagate and cure by addition reactions to form high molecular weight, thermally stable compositions.

Another object of the invention is to provide ethynyl end-capped quinoxaline oligomers.

A further object of the invention is to provide a process for synthesizing ethynyl end-capped quinoxaline oligomers.

Still another object of the invention is to provide quinoxaline oligomers which are soluble in low boiling organic solvents, exhibit low softening points, and cure in a short period of time.

A still furher object of the invention is to provide quinoxaline oligomers which can be readily cured in a rapid manner to high molecular weight polymers having superior physical properties and possessing a high degree of thermal oxidative stability.

Other objects and advantages of the invention will become apparent to those skilled in the art upon consideration of the ensuing disclosure and the drawing which is a graph demonstrating the thermal oxidative stability of a cured quinoxaline oligomer of this invention.

SUMMARY OF THE INVENTION

The present invention resides in ethynyl terminated aromatic polyphenylquinoxaline compositions which cure by addition reactions. (The compositions are also referred to herein as ethynyl terminated polyquinoxalines and ethynyl end-capped quinoxaline oligomers.) The compositions of this invention can be represented by the following structural formula:

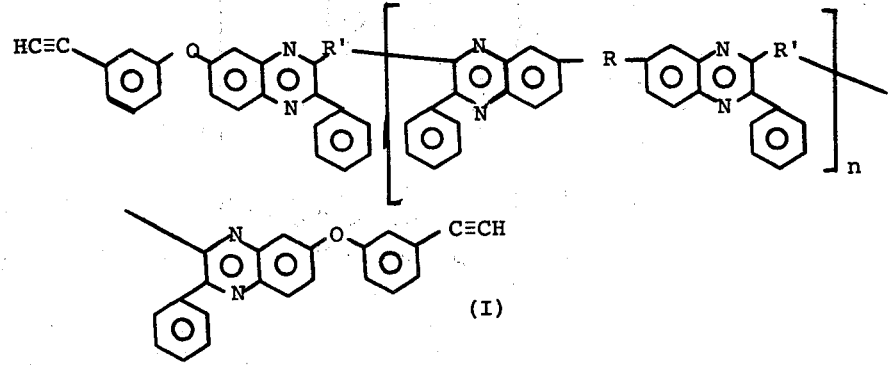

(I)

where R is a single bond,

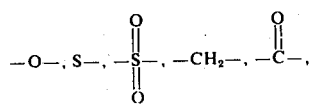

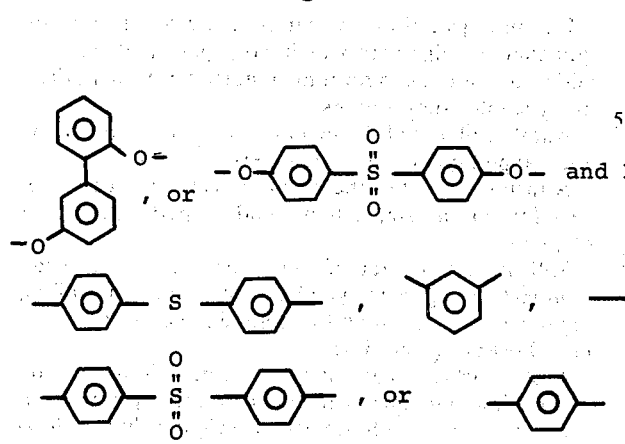, or 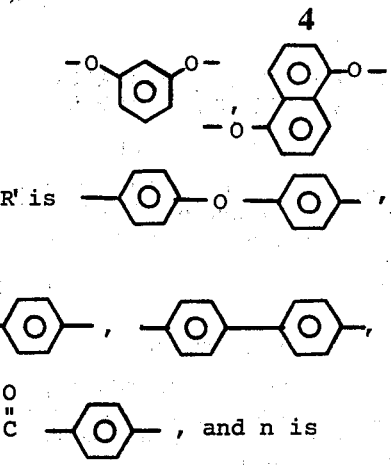 and R' is and n is an integer from 1 to 20, inclusive.

In another embodiment, the invention resides in a process for synthesizing the ethynyl end-capped quinoxaline oligomers by reacting in the presence of a catalytic amount of glacial acetic acid an aromatic bis(o-diamine) (II) with an excess of an aromatic bisbenzil (III), thereby providing a benzil end-capped quinoxaline oligomer (IV) which is then reacted in the presence of a catalytic amount of glacial acetic acid with 4-(3-ethynylphenoxy)orthophenylene diamine (V). The reactions involved can be represented by the equations set forth below in which the Roman numerals refer to the compositions indicated in the preceding sentence and the Roman numeral (I) designates the ethynyl end-capped quinoxaline oligomer whose structural formula is shown above.

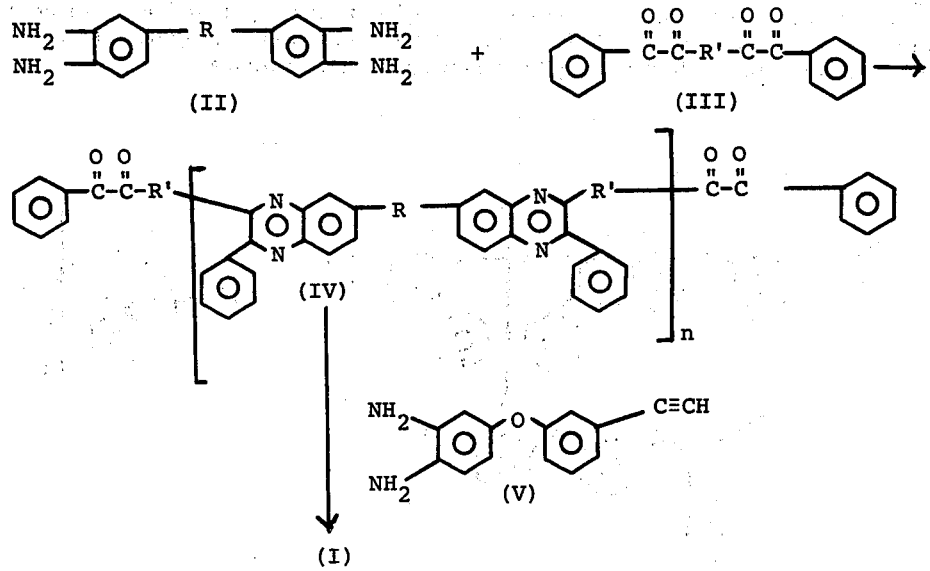

In the foregoing formula, R, R' and n are as indicated hereinabove. As seen from the foregoing, the R and R' groups of the benzil endcapped quinoxaline oligomers (IV) and the ethynyl end-capped quinoxaline oligomers (I) are derived from the aromatic bis(o-diamine) (II) and the aromatic bisbenzil (III), respectively.

The aromatic bis(o-diamines) and the aromatic bisbenzils employed in the process are well known compounds that are described in the literature. Examples of bis(o-diamines) include 3,3',4,4'-tetraaminobiphenyl; 3,3',4,4'-tetraaminodiphenylether; 3,3',4,4'-tetraaminodiphenylsulfide; 3,3',4,4'-tetraaminodiphenylsulfone; 3,3',4,4'-tetraaminodiphenylmethane; 3,3',4,4'-tetraaminobenzophenone; 1,3-bis(3,4-diaminophenoxy)benzene; 2,2'-bis(3,4-diaminophenoxy)biphenyl; 1,5-bis(3,4-diaminophenoxy)naphthalene; 4,4'-bis(3,4-diaminophenoxy)-diphenylsulfone; and the like. Examples of aromatic bisbenzils include 4,4'-(phenylglyoxaloyl)diphenylether; 4,4'-(phenylglyoxaloyl)-diphenylsulfide; 1,3-(phenylglyoxaloyl)benzene; 1,4-(phenylglyoxaloyl)benzene; 4,4'-(phenylglyoxaloyl)biphenyl; 4,4'-(phenylglyoxaloyl)diphenylsulfone; 4,4'-(phenylglyoxaloyl)benzophenone; and the like.

As mentioned above, in preparing the ethynyl terminated polyquinoxalines, in the first step of the process an aromatic bis(o-diamine) is reacted with a molar excess of an aromatic bisbenzil. Generally from about 0.10 to 1 mole of the bis(o-diamine) is reacted with 2 moles of the bisbenzil. When the mole ratio of bisbenzil to bis(o-diamine) is 2 to 1, the value of n in the above equation is 1. As the ratio increases, i.e., greater amounts of bisbenzil as compared to bis(o-diamine) are used, the value of n in the equation also increases. The number of moles of the endcapping agent, 4-(3-ethynylphenoxy)orthophenylene diamine, used in the second step of the process is usually equal to the number of moles of the bisbenzil employed in the first step. However, it is within the scope of the invention to use a molar excess of the end-capping agent, e.g., 1 to 1.25 mole of end-capping agent per mole of bisbenzil.

In carrying out the process, m-cresol is utilized as the reaction medium. m-Cresol is used in an amount sufficient to give a stirrable reaction mixture and can be readily determined by one skilled in the art. The first and second steps of the process are conducted in the presence of a catalytic amount of glacial acetic acid. The amount of catalyst used can vary within rather wide limits, but it usually ranges from about 0.5 to 10 volume percent of the m-cresol. The temperatures at which the reactions are conducted generally fall in the range of 80° to 190°C although it is preferred to operate under reflux conditions. The total period for the reactions usually ranges from 10 minutes to 2 hours. The reactions are conducted under a blanket of an inert gas, such as nitrogen, helium or argon.

Upon completion of the reaction period, the oligomer is recovered and purified by a general procedure that is conventionally followed in solution polymerization processes. Thus, the reaction mixture is poured into a non-solvent for the polyquinoxaline, e.g., into an alcohol such as methanol, thereby causing the oligomer to precipitate from solution. The precipitated oligomer is separated from the liquid by any suitable means, such as by filtration or decantation. The separated oligomer is then dissolved in a solvent, such as methylene chloride, and again precipitated from solution by pouring the solution into methanol. After separation of the precipitated polymer, it is dried by boiling off the methylene chloride. It is to be understood that this procedure can be repeated one or more times in order to further purify the product.

Curing of the ethynyl terminated polyquinoxalines is readily accomplished by heating the oligomers in an inert or oxidative atmosphere at a temperature ranging from about 200° to 370°C. A heating period of from about 1 to 2 hours is usually sufficient to obtain a complete cure although longer times, e.g., up to 24 hours, can be used. While it is not intended to be limited to any particular theory, in the curing operation it is believed that the terminal ethynyl groups propagate in a linear fashion by Strauss coupling and/or a Diels Alder reaction as well as crosslinking by a trimerization reaction to form benzene rings. The reactions that are believed to be involved are shown by the following equations:

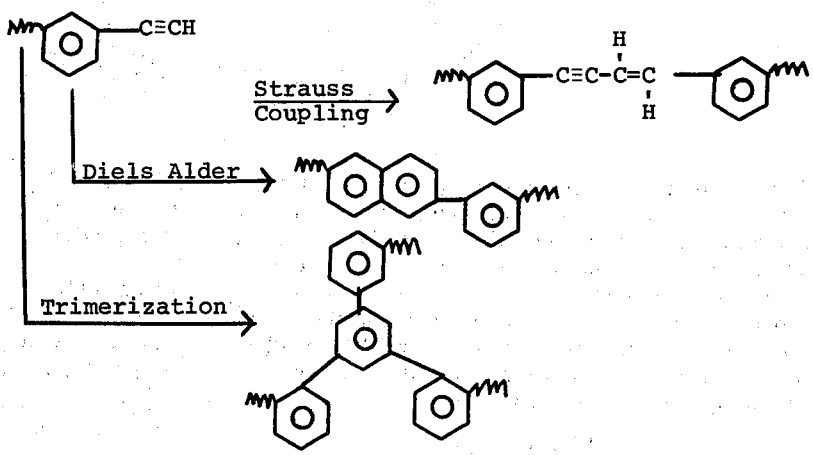

The cured oligomers possess excellent thermooxidative stability. This outstanding property is shown by FIG. 1 which is a graph of data obtained when a cured oligomer of this invention was isothermally aged in circulating air at 600°F. After 100 hours of aging, the cured oligomer had lost only about 8 percent of its initial weight while after 200 hours the weight loss was still only about 13 percent.

As previously mentioned, the aromatic bis(o-diamines) and the aromatic bisbenzils used in the present process are well known compounds. However, the 4-(3-ethynylphenoxy)-o-phenylenediamine (V), which functions as an end-capping agent, is a new composition which is synthesized by a four-step procedure. Firstly, 3,4-dinitrofluorobenzene (VI) is reacted with the sodium salt of m-hydroxyacetophenone (VII) to give 3'-acetylphenyl-3,4-dinitrophenyl ether (VIII). The acetyl group of (VIII) is then converted to a chlorocinnamaldehyde group by treating with oxalyl chloride in dimethylformamide (DMF) to give m-(3,4-dinitrophenoxy)-α-chlorocinnamaldehyde (IX). Hydrolysis of (IX) with sodium hydroxide gives 4-(3-ethynylphenoxy)-o-dinitrobenzene (X) which is reduced to 4-(3-ethynylphenoxy)-o-phenylenediamine (XI). The described synthesis of (XI) is shown by the following equations:

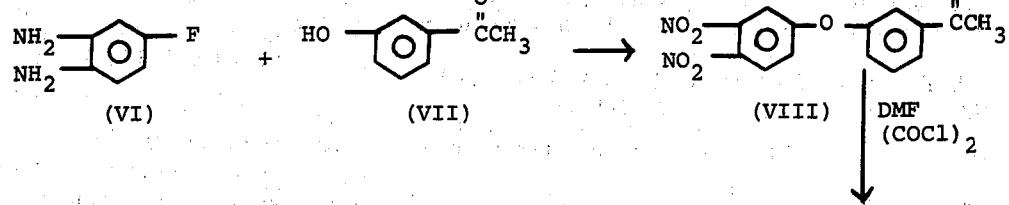

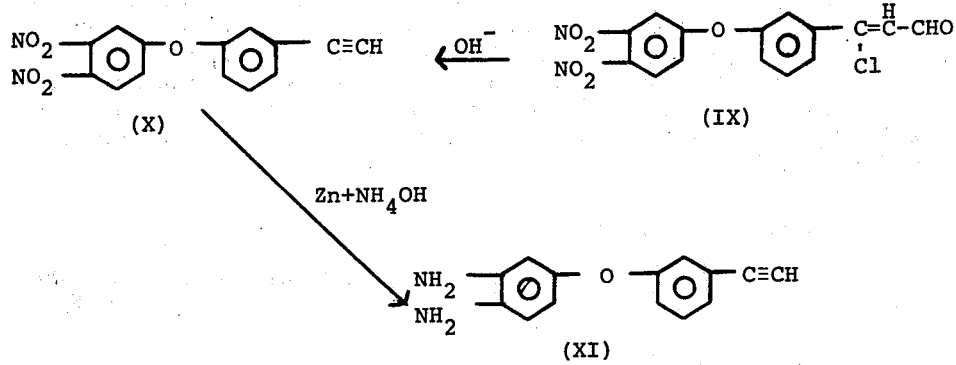

A more complete discussion of the synthesis of 4-(3-ethynylphenoxy)-o-phenylenediamine is included in our copending application U.S. Ser. No. 578,847, filed on May 19, 1975, the disclosure of which is incorporated herein by reference.

A more comprehensive understanding of the invention can be obtained by referring to the following illustrative examples which are not intended, however, to be unduly limitative of the invention.

EXAMPLE 1

Preparation of 4-(3-ethynylphenoxy)-o-phenylenediamine (a) 3'-Acetyl-3,4-dinitrophenyl ether (VIII)

To a solution containing 8.0 g (67 mmoles) of m-hydroxyacetophenone dissolved in 50 ml of dry pyridine was added 2.8 g (approximately 67 mmoles) of solid sodium hydride (57% dispersion in mineral oil). The resulting mixture (frothing) was stirred at room temperature for 3 hours, at which time the flask was cooled to 0°, and 15 g (75 mmoles) of solid 3,4-dinitrofluorobenzene was added all at once. The reaction mixture was allowed to warm to room temperature, and was then heated at 100°C for an additional hour. The contents of the flask were then poured into one liter of water and the resulting mixture extracted with two 100 ml portions of methylene chloride. The combined extracts were washed with two portions of 5% HCl solution and the organic phase evaporated to a volume of 50 ml. The concentrated solution of crude product was filtered through a 2 × 4 dry column of silica gel (Voelm) which was eluted with methylene chloride. The eluate was evaporated to dryness, and the residue rechromatographed on a 2 × 12 inch dry column of silica gel. Elution with 1:1 methylene chloride:hexane removed a first band of impurities. Further elution using methylene chloride produced a second band containing the product. Evaporation of the eluate to dryness, and recrystallization of the residue from methylene chloride/absolute ethanol afforded 11.7 g (58%) of yellow crystals, m.p. 140°–141°C. Large crystals of high purity material were obtained by slow spontaneous evaporation of concentrated methylene chloride solutions of (VIII).

Analysis: Calc'd for $C_{14}H_{10}N_2O_6$: C,55.65; H,3.31; N,9.27. Found: C,55.43; H,3.29; N,9.29.

(b) m-(3,4-Dinitrophenoxy)-α-chlorocinnamaldehyde (IX)

A 250 ml 1-neck, round-bottomed flask equipped with magnetic stirrer and nitrogen adapter was thoroughly flamed and purged with nitrogen. To the flask was added 25 ml of dry dimethylformamide (DMF) and the flask was cooled to 0°C in an ice bath. Oxalyl chloride (2.5 g – 20 mmoles) was added dropwise to the flask (fuming) under nitrogen over a period of ½ hour, producing a white precipitate of Vilsmeyer complex. After the addition, the reaction mixture was stirred at 0°C for an additional ½ hour, at which time a solution containing 5.0 g (16.5 mmoles) of 3-acetylphenyl-3,4-dinitrophenyl ether dissolved in 25 ml of dry DMF was added dropwise while maintaining the bath temperature at 0°C. The cooling was then removed, and the reaction mixture stirred at room temperature for one hour, and then at 50°C for an additional hour. The contents of the flask were poured into 500 ml of cold, saturated sodium bicarbonate solution, and the crude product which precipitated was extracted into methylene chloride. The combined extracts were evaporated to a small volume and filtered through a 1 × 4 inch dry column of silica gel, eluting with additional methylene chloride. Evaporation of the elute to dryness yielded (IX) as the product in the form of a yellow powder, m.p., 100°–101°C (40%).

Analysis: Calc'd for $C_{15}H_9N_2O_6Cl$: C, 51.07; H,2.60; N,8.03; Cl. 10.17. Found: C,51.49; H,2.52; N,7.97; Cl, 9.98.

(C) 4-(3-Ethynylphenoxy)-o-dinitrobenzene (X)

To 50 ml of refluxing 1N sodium hydroxide solution, under a nitrogen atmosphere, was added a solution containing 10 g (0.028 mole) of (IX) dissolved in 50 ml of 1,4-dioxane. The dark mixture was refluxed for ½ hour at which time the solution was cooled and acidified with 10% sulfuric acid. The reaction mixture was extracted with several 50 ml portions of ether, and the combined extracts evaporated to dryness. The residue was chromatographed on a 1 × 12 inch dry column of silica gel. Elution of the column using 3/1 hexane/methylene chloride produced a first band of side-product. Further elution using 1/1 hexane/methylene chloride yielded a second band which contained the desired product. Evaporation of the eluate to dryness in vacuo afforded 2 g (25%) of (X) as light yellow crystals, m.p., 68°–69°C.

Analysis: Calc'd for $C_{14}H_8O_5$: C,59.16; H,2.84; N,9.86. Found: C,59.01; H,2.82; N,9.85.

(d) 4-(3-Ethynylphenoxy)-o-phenylenediamine (XI)

To a rapidly stirred suspension of 25 g (0.38 g atom) of powdered zinc in 25 ml of concentrated ammonium hydroxide was added a solution containing 5.0 g (17.6 mmoles) of (X) dissolved in 25 ml of tetrahydrofuran. The mixture was stirred at room temperature for one-half hour at which time an additional 5 ml of ammonium hydroxide was added, and the solution was stirred an additional half hour. At that time, the reaction mixture was filtered by suction, and the residue was washed with several portions of tetrahydrofuran. The filtrate was extracted with several portions of ether, and the combined ether extracts washed with water. Evaporation of the organic layer in vacuo yielded a dark red oil. Chromatography of the residue on 1 × 12 inch dry column of silica gel afforded an initial red band (elution with methylene chloride) of side-product. Further elution using ethyl acetate produced a second band of desired product. Evaporation of solvent in vacuo yielded 3.3 g (84%) of (XI) as a dark orange oil.

Analysis: Calc'd for $C_{14}H12N_2O$: C,74.98; H,5.39; H,12.49. Found: C,74.43; H,5.31; N,11.98.

EXAMPLE II

Preparation of end-capped oligomer from 3,3'-diaminobenzidine and 4,4'-(phenylglyoxaloyl)diphenylether.

To a rapidly stirred solution containing 10.2 g (23 mmoles) of 4,4'-(phenylglyoxaloyl)diphenylether and 5 ml of glacial acetic acid in 50 ml of m-cresol was slowly added, under a nitrogen atmosphere, a solution containing 2.5 g (11.7 mmoles) of 3,3'-diaminobenzidine dissolved in 50 ml of m-cresol. After completion of the addition, the reaction mixture was heated at reflux for one hour, at which time a distilling apparatus was attached to the reaction flask, and m-cresol was distilled until one-half of the original volume remained.

To the cooled solution was added 10 ml of glacial acetic acid, followed by a solution containing 5.6 g (25 mmoles) of 4-(3-ethynylphenoxy)-orthophenylenediamine dissolved in 20 ml of m-cresol. The mixture was stirred at room temperature for ½ hour and then heated to reflux for 15 minutes during which time m-cresol was distilled from the flask to decrease the volume of the solution to 35 ml. The cooled reaction mixture was then added dropwise to 2 liters of stirred methanol, causing precipitation. The yellow end-capped oligomer was twice reprecipitated from methylene chloride into methanol with the methylene chloride being boiled away each time yielding 15 g (91%) of oligomer.

Analysis: Calc'd for $(C_{96}H_{58}N_8O_4)_n$ where $n=1$: C,83.10; H,4.21; N,8.08. Found: C,81.32; H,4.05; N,7.82.

EXAMPLE III

Preparation of end-capped oligomer from 3,3'-diaminobenzidine and 4,4'-(phenylglyoxaloyl)diphenylsulfide To a rapidly stirred solution containing 2.1 g (4.7 mmoles) of 4,4'-(phenylglyoxaloyl)diphenylsulfide and 1 ml of glacial acetic acid dissolved in 25 ml of m-cresol was slowly added, under a nitrogen atmosphere, a solution containing 0.5 g (2.33 mmoles) of 3,3'-diaminobenzidine dissolved in 25 ml of m-cresol. After completion of the addition, the reaction mixture was heated at reflux for one hour, at which time one-half of the m-cresol was distilled out of the reaction mixture. To the cooled reaction mixture was added 1 ml of glacial acetic acid, followed by a solution containing 1.05 g (4.7 mmoles) of 4-(3-ethynylphenoxy)-orthophenylenediamine dissolved in 10 ml of m-cresol. The mixture was stirred at room temperature for ½ hour and then heated to reflux for 15 minutes during which time m-cresol was distilled from the flask to decrease the volume of the solution to 10 ml. The cooled reaction mixture was then added dropwise to 100 ml of stirred methanol, causing precipitation. The yellow end-capped oligomer was twice reprecipitated from methylene chloride into methanol with the methylene chloride being boiled away each time yielding 3.3 g (99%) of oligomer.

Analysis: calc'd for $(C_{96}H_{58}N_8S_2O_2)_n$ where $n=1$: C,81.21; H,4.11; N,7.90. Found: C,80.50; H,3.98; N,7.45.

EXAMPLE IV

Preparation of end-capped oligomer from 3,3'-diaminobenzidine and 1,4-(phenylglyoxaloyl)benzene To a rapidly stirred solution containing 0.64 g (1.87 mmoles of 1,4-(phenylglyoxaloyl)benzene and 1 ml of glacial acetic acid dissolved in 25 ml of m-cresol was slowly added, under a nitrogen atmosphere, a solution containing 0.2 g (0.93 mmole) of 3,3'-diaminobenzidine dissolved in 25 ml of m-cresol. After completion of the addition, the reaction mixture was heated at reflux for one hour, at which time one-half of the m-cresol was distilled out of the reaction mixture. To the cooled reaction mixture was added 1 ml of glacial acetic acid, followed by a solution containing 0.47 g (1.87 mmoles) of 4-(3-ethynylphenoxy)-orthophenylenediamine dissolved in 10 ml of m-cresol. The mixture was stirred at room temperature for ½ hour and then heated to reflux for 15 minutes during which time m-cresol was distilled from the flask to decrease the volume of the solution to 10 ml. The cooled reaction mixture was then added to 100 ml of stirred methanol, causing precipitation. The yellow end-capped oligomer was twice reprecipitated from methylene chloride into methanol with the methylene chloride being boiled away each time, yielding 1.05 g (96%) of the oligomer.

Analysis: Calc'd for $(C_{84}H_{50}N_8O_2)_n$ where $n=1$: C,83.83; N,4.18; N,9.31. Found: C,82.98; H,3.85; N,9.01.

EXAMPLE V

Cure Reactions of Oligomers of Example II, III and IV

Small samples of neat resin prepared in Examples II, III, and IV were placed into small test tubes. The tubes were flushed with nitrogen and then were placed in a preheated metal block. After various time periods and temperatures, the tubes were removed and allowed to cool. The glass transition temperatures of the cured resins were then determined by thermomechanical analysis. The data obtained are shown below in Table I.

TABLE I

| Oligomer | Softening[1] Point, °C | Cure Temperature, °C | Time at Cure Temp, hr. | Tg After Cure, °C |
|---|---|---|---|---|
| II | 154 | 280 | ½ | 312 |
| II | — | 280 | 2 | 317 |
| III | 144 | 280 | 6 | 321 |
| IV | 161 | 280 | 6 | 332 |

[1]Softening points were determined using the Perkin Elmer Differential Scanning Calorimeter.

EXAMPLE VI

Molded films were fabricated using oligomer of Example II. Neat resin samples were placed between aluminum foil and set in a preheated (various cure temperatures) press and molded at 200 psi. Room temperature tensile strength as a function of time and cure temperatures are listed below in Table II.

TABLE II

| Film No. | Cure Temp, °C | Time at Cure Temp, hr | Tensile Strength psi | Elongation To Break, % |
|---|---|---|---|---|
| 1 | 280 | 5 | 5022 | 2.7 |
| 2 | 316 | 1 | 5942 | 2.8 |
| 3 | 316 | 5 | 6546 | 2.7 |
| 4[(1)] | 316 | 1 | — | — |
|  | 371 | 1 | 15,000 | 2.3 |

[(1)]Film (4) was postcured for 1 hour at 371°C.

The optimum cure conditions for the resin, from the standpoint of mechanical performance, was one hour at 316°C and one hour postcure at 371°C.

As seen from the data in the foregoing examples, the ethynyl terminated quinoxaline oligomers can be readily cured in a short period of time. Because of the curing mechanism, volatile by-products are not evolved, thereby eliminating the presence of voids in the cured products. The cured oligomers have a high glass transition temperature (Tg), an important property for polymers which may be subjected to high temperatures.

The ethynyl end-capped polyquinoxalines are extremely soluble in low-boiling solvents, such as methylene chloride, tetrahydrofuran and dioxane. This property of the oligomers renders the material ideally suitable for use in the fabrication of solvent-free prepregs and void-free structural composites. The low softening points (140°–160°C) of the oligomers also facilitates low processing temperatures in the fabrication of structural reinforced composites.

As will be evident to those skilled in the art, modifications of the present invention can be made in view of the foregoing disclosure without departing from the spirit and scope of the invention.

We claim:

1. An ethynyl terminated polyquinoxaline having the following structural formula:

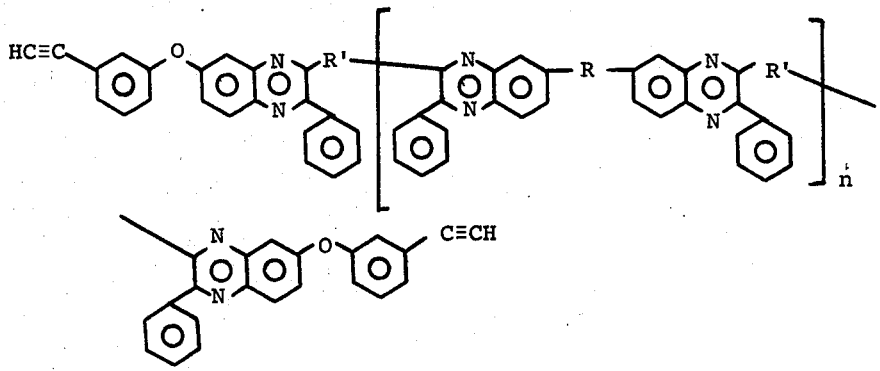

where R is a single bond,

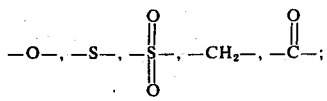

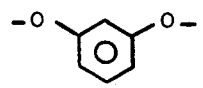

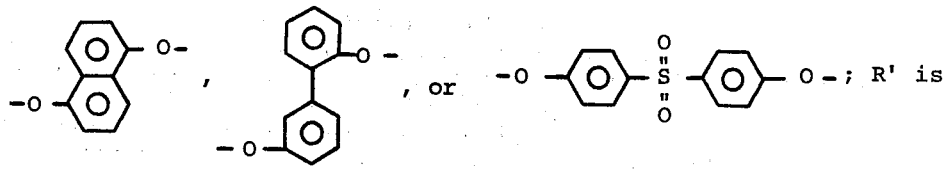

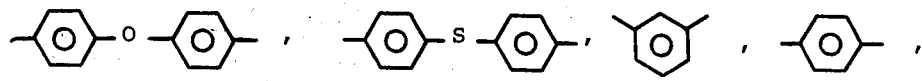

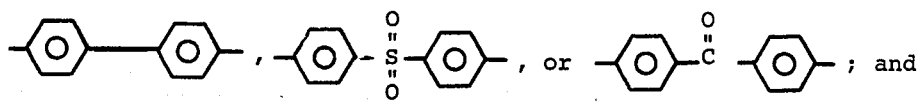

and $n$ is an integer from 1 to 20, inclusive.
2. The polyquinoxaline of claim 1 in which R is a single bond and R' is
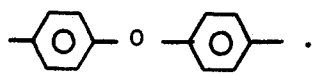
3. The polyquinoxaline of claim 1 in which R is a single bond and R' is
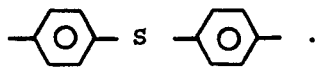
4. The polyquinoxaline of claim 1 in which R is a single bond and R' is
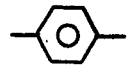
5. The polyquinoxaline of claim 1 in which R is —O— and R' is
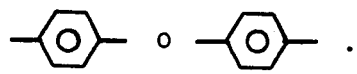
6. The polyquinoxaline of claim 1 in which R is —O— and R' is
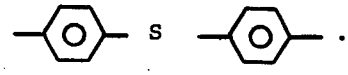
* * * * *